US011710557B2

(12) United States Patent
Birtwhistle

(10) Patent No.: US 11,710,557 B2
(45) Date of Patent: Jul. 25, 2023

(54) METHOD FOR CONFIGURING DIABETES MANAGEMENT DEVICE BY HEALTHCARE PROVIDER

(71) Applicant: ROCHE DIABETES CARE, INC., Indianapolis, IN (US)

(72) Inventor: Daniel P. Birtwhistle, Fishers, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 533 days.

(21) Appl. No.: 16/071,535

(22) PCT Filed: Jan. 20, 2017

(86) PCT No.: PCT/EP2017/051188
§ 371 (c)(1),
(2) Date: Jul. 20, 2018

(87) PCT Pub. No.: WO2017/125550
PCT Pub. Date: Jul. 27, 2017

(65) Prior Publication Data
US 2019/0035495 A1 Jan. 31, 2019

Related U.S. Application Data

(60) Provisional application No. 62/281,988, filed on Jan. 22, 2016.

(51) Int. Cl.
*G16H 40/40* (2018.01)
*G16H 20/10* (2018.01)
(Continued)

(52) U.S. Cl.
CPC ......... *G16H 40/40* (2018.01); *A61B 5/14532* (2013.01); *G16H 20/10* (2018.01); *G16H 80/00* (2018.01); *G16H 20/17* (2018.01)

(58) Field of Classification Search
None
See application file for complete search history.

(56) References Cited

U.S. PATENT DOCUMENTS

2005/0283198 A1 12/2005 Haubrich et al.
2008/0262469 A1* 10/2008 Brister .................. A61M 5/24
604/504

(Continued)

FOREIGN PATENT DOCUMENTS

WO WO-2007019446 A2 * 2/2007 ......... G06F 19/3418

OTHER PUBLICATIONS

Ventola C. L. (2014). Mobile devices and apps for health care professionals: uses and benefits. P & T : a peer-reviewed journal for formulary management, 39(5), 356-364. (Year: 2014).*

(Continued)

*Primary Examiner* — Lena Najarian
(74) *Attorney, Agent, or Firm* — Harness, Dickey & Pierce, P.L.C.

(57) ABSTRACT

The present disclosure relates to a device configuration method for configuring a diabetes management device by a diabetes management system, the diabetes management system residing on a server computer, the method comprising: receiving, by the diabetes management system, a therapy setting instruction from a computing device, validating, by the diabetes management system, the credentials of the healthcare provider by way of a validation service based on the identification information, determining, by the diabetes management system, whether the therapy setting instruction is valid based on an association between the diabetes management system, the patient, and the healthcare provider; transmitting, by the diabetes management system, one or more parameters for configuring the feature defined by the therapy setting to the subject diabetes management device; and canceling, by the diabetes management system, (Continued)

the therapy setting instruction in response to the therapy setting instruction being invalid. Further, a method for issuing a prescription for configuring a diabetes management device by way of a prescription system and a diabetes management system, and a diabetes management system for processing a therapy setting instruction issued by a computing device operated by a healthcare provider is provided.

11 Claims, 7 Drawing Sheets

(51) Int. Cl.
*G16H 80/00* (2018.01)
*A61B 5/145* (2006.01)
*G16H 20/17* (2018.01)

(56) References Cited

U.S. PATENT DOCUMENTS

| | | | |
|---|---|---|---|
| 2013/0036415 A1 | 2/2013 | Birtwhistle | |
| 2013/0070090 A1* | 3/2013 | Bufalini | G16H 20/13 348/143 |
| 2014/0325065 A1* | 10/2014 | Birtwhistle | G16H 40/67 709/225 |

OTHER PUBLICATIONS

International Search Report and Written Opinion of the International Searching Authority issued in PCT/EP2017/051188, dated May 10, 2017; ISA/EP.

* cited by examiner

METHOD FOR CONFIGURING DIABETES MANAGEMENT DEVICE BY HEALTHCARE PROVIDER

CROSS REFERENCE TO RELATED APPLICATIONS

This application is a U.S. National Phase Application under 35 U.S.C. 371 of International Application No. PCT/EP2017/051188 filed on Jan. 20, 2017 and published in English as WO 2017/125550 A1 on Jul. 27, 2017. This application is based on and claims the benefit of priority from U.S. Provisional Patent Application No. 62/281,988 filed Jan. 22, 2016. The entire disclosures of all of the above applications are incorporated herein by reference.

The present disclosure relates to a method for configuring a diabetes management device.

BACKGROUND

For people with diabetes, successful management of one's condition requires monitoring the effects lifestyle changes can have in both the short term and the long term. An individual with diabetes may use one or more diabetes management devices for tracking and monitoring their condition. For example, the individual may carry specialized electronic devices that allow the individual to periodically measure their glucose levels using a blood glucose meter and take appropriate action, such as administering insulin using an insulin pump. More recently, diabetes management applications have been developed to help the individual track lifestyle changes. Such applications may be used to collect information regarding the individual's meals, glucose measures, drug dosage, exercise, and other suitable information. In addition, the application may allow the individual to perform various structured tests that analyze the data being stored.

A patient with diabetes may wish to share results and/or data from their diabetes management devices with a healthcare provider. Based on the results, the healthcare provider may wish to have the patient adjust the operation of their diabetes management device. For example, the healthcare provider may like to perform a structured test using the patient's blood glucose monitor or adjust a target blood glucose level of a bolus calculator provided with an insulin pump.

This section provides background information related to the present disclosure which is not necessarily prior art.

SUMMARY

A device configuration method for configuring a diabetes management device by a diabetes management system according to claim 1 is provided. According to a further aspect, a method for issuing a prescription for configuring a diabetes management device by way of a prescription system and a diabetes management system according to claim 12 is provided. According to another aspect, a diabetes management system for processing a therapy setting instruction issued by a computing device operated by a healthcare provider according to claim 17 is provided.

The device configuration method may be further comprising:
  comparing, by the diabetes management system, the recipient information provided in the therapy setting instruction with a profile information of one or more registered members stored in a registry, wherein the diabetes management system includes the registry;
  classifying, by the diabetes management system, the patient as a subject registered member in response to the recipient information corresponding with the profile information of at least one of the one or more registered members; and
  identifying, by the diabetes management system, the therapy setting instruction as invalid in response to the recipient information not corresponding with the profile information of at least one of the one or more registered members.

The device configuration method may be further comprising: determining, by the diabetes management system, whether the healthcare provider is authorized by the subject registered member to issue the therapy setting instruction in response to the recipient being registered with the diabetes management system, wherein the diabetes management system is operable by the subject registered member to identify an authorized healthcare provider and the diabetes management system stores information to associate the authorized healthcare provider with the subject registered member; and
identifying, by the diabetes management system, the therapy setting instruction as invalid in response to the healthcare provider not being authorized by the subject registered member.

The device configuration method may be further comprising:
  determining, by the diabetes management system, whether the subject diabetes management device identified is registered with the diabetes management system by the subject registered member in response to the recipient being registered with the diabetes management system, wherein the diabetes management system is operable by the subject registered member to register a given diabetes management device and the diabetes management system stores information regarding the given diabetes management device with the profile information of the subject registered member; and
  identifying, by the diabetes management system, the therapy setting instruction as invalid in response to the diabetes management device not being registered with the diabetes management system.

The device configuration method may be further comprising:
  prior to transmitting the one or more parameters, issuing, by the diabetes management system, a device configuration notification to the subject diabetes management device in response to the credentials of the healthcare provider being valid and the therapy setting instruction being valid, wherein the device configuration notification notifies the user of the subject diabetes management device that the healthcare provider has issued the therapy setting and requests the user to either accept or decline the therapy setting; and
  receiving, by the diabetes management system, a message from the subject diabetes management via the communication network, wherein the message indicates whether the user accepts or declines the therapy setting; and
  canceling, by the diabetes management system, the therapy setting instruction in response to the message indicating the user declined the therapy setting instruction, wherein the diabetes management system transmits the one or more parameters in response to the message indicating the user accepted the therapy setting instruction.

The device configuration method may further comprise notifying, by the diabetes management system, the healthcare provider of a status of the therapy setting instruction, wherein the status of the therapy setting is designated as an accepted therapy setting in response to the therapy setting being accepted by the user, the status of the therapy setting is designated as a declined therapy setting in response to the therapy setting being declined by the user, and the status of the therapy setting is designated as invalid in response to the credentials of the healthcare provider being invalid.

The identification information may include at least one of a name of the healthcare provider and a license number of the healthcare provider.

The diabetes management device may be a medical device.

The diabetes management device may be a portable computing device that has a diabetes management application residing in the portable computing device.

The therapy setting instruction may be determined as invalid in response to the credentials of the healthcare provider being invalid.

The diabetes management system may be paired with the subject diabetes management device before transmitting the one or more parameters such that the diabetes management system and the subject diabetes management device may automatically communicate via the communication network.

The method may be further comprising determining, by the diabetes management system, the prescription as invalid in response to the therapy setting being declined by the user.

With regard to the method, prior to issuing the device configuration notification, the method may further comprise: determining, by the diabetes management system, whether the healthcare-provider is authorized by the patient to issue the therapy setting in response the patient being identified as the subject registered member; and identifying, by the diabetes management system, the prescription as invalid in response to the healthcare provider not being authorized to issue the therapy setting; wherein the device configuration notification is issued in response to the patient being identified as the subject registered member and the healthcare provider being authorized to issue the therapy setting.

The prescription system may be different from the diabetes management system.

With regard to the method, prior to issuing the device configuration notification, the method may further comprise:
 identifying, by the diabetes management system, the diabetes management device to be configured based on the therapy setting;
 comparing, by the diabetes management system, the diabetes management device identified with one or more registered devices associated with the subject registered member in response to the patient being identified as the subject registered members; and
 determining, by the diabetes management system, the prescription as invalid in response to the diabetes management device identified not being associated with at least one of the registered devices, wherein the device configuration notification is issued in response to the diabetes management device identified being associated with at least one of the registered devices.

With regard to the diabetes management system, the validation module may validate credentials of the healthcare provider by way of a third party validation service, and the validation module may identify the therapy setting instruction as invalid in response to the credentials of the healthcare provider being invalid.

For the diabetes management system the following may be provided:
 the validation module determines whether the patient identified in the recipient information is a registered member based on one or more profile information stored in a registry,
 the validation module determines whether the patient authorized the healthcare provider to issue the therapy setting in response to the patient being the registered member, and
 the validation module identifies the therapy setting instruction as invalid in response to the patient not being the registered member or the healthcare provider not being authorized by the patient to issue the therapy setting instruction.

With regard to the diabetes management system, the following may be provided:
 the validation module determines whether the patient identified in the recipient information is a registered member based on one or more profile information stored in a registry,
 the device update module identifies the diabetes management device to be configured based on the therapy setting instruction,
 the device update module determines whether the diabetes management device identified is a registered device by the patient that is determined as the registered member by the validation module, and
 the device update module identifies the therapy setting instruction as invalid in response to the diabetes management device identified not being the registered device.

The diabetes management device may be a medical device. The diabetes management device may be a portable computing device that has a diabetes management application residing in the portable computing device.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
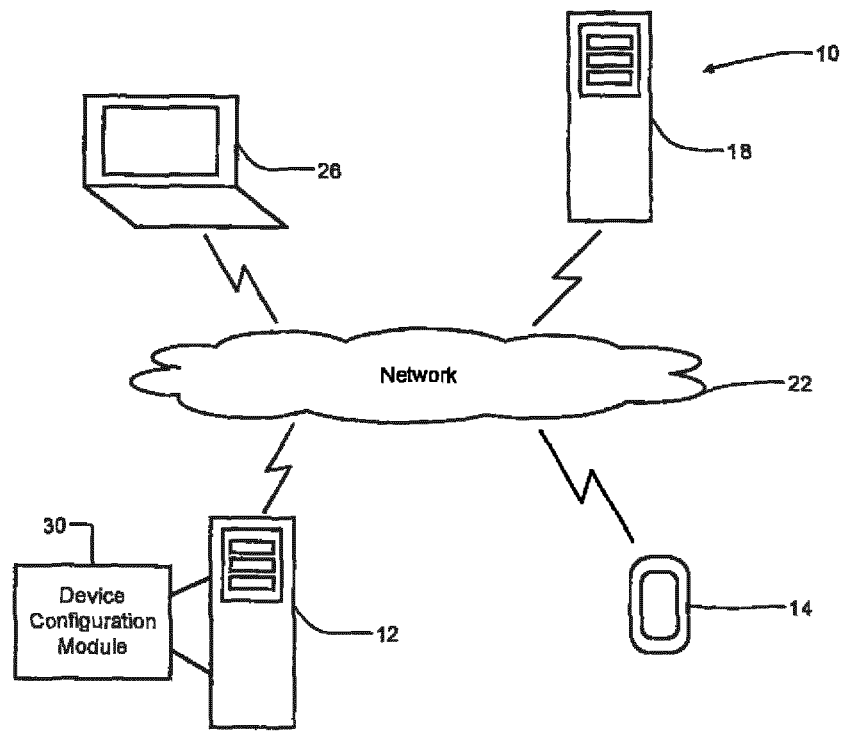
FIG. 1 illustrates a therapy setting system that includes a diabetes management system in data communication with external devices.
Figure 2:
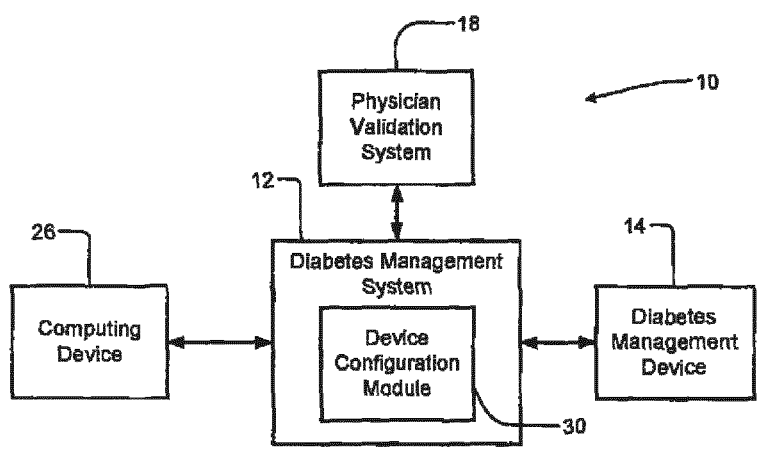
FIG. 2 is a block diagram of a therapy setting system that includes the diabetes management system and a physician validation system in a first embodiment.

The present disclosure will now be described more fully with reference to the accompanying drawings. With reference to FIGS. 1 and 2, a first embodiment of a therapy setting system 10 is presented. The therapy setting system 10 includes a diabetes management system 12. The therapy setting system 10 enables a healthcare provider to configure a diabetes management device 14 of a patient that is under the care of the healthcare provider by way of the diabetes management system 12. Before configuring the diabetes management device 14, the diabetes management system 12 validates the credentials of the healthcare provider through a physician validation system 18.

The diabetes management system 12 may be housed in one or more servers. The diabetes management system 12 may communicate with external devices via a communication network 22, such as the internet. The diabetes management system 12 may include various software tools available to a user for managing diabetes. For example, the diabetes management system 12 may include a logbook for tracking blood glucose measures, insulin dosage, meal information, physical activity, and/or other suitable information used to monitor diabetes.

The diabetes management device 14 may include a computer processor, memory, and/or transceiver for communicating with external devices. The diabetes management device 14 is an electronic device that is capable of diagnosing, monitoring, and/or treating diabetes. As an example, the diabetes management device 14 may be a medical device, such as an insulin pump a blood glucose monitor, and/or other suitable instrument for diagnosing and/or treating diabetes. The medical device may support multiple operation features available to a user. Each feature may include one or more parameters that may be configured to control the operation of the feature. For example, a feature of a blood glucose monitor may include the execution of one or more structured tests, such as testing in pairs (TiP) and a three-day profile structured test. Parameters of the structured test may include start time of testing, notification for taking blood glucose measurement, and other suitable settings of a structured test.

As another example, an insulin pump may support the following features: administration of insulin, a bolus calculator, and/or monitoring blood glucose level. Example parameters for one or more of the features of the insulin pump may include insulin dosage, target blood glucose level, insulin to carbohydrate ratio, insulin to blood glucose measure ratio, maximum bolus, and/or blood glucose measurement time.

The diabetes management device 14 may also be a portable computing device that has a diabetes management software application residing in the portable computing device. The portable device may be, for example, a tablet, a smartphone, and/or a computer. The diabetes management application may be implemented as computer executable instructions executed by a computer processor of the portable computing device. The diabetes management application may include multiple tools for monitoring diabetes. As an example, the diabetes management application may include the following features that are accessible by a user: a logbook, a bolus calculator, automatic data syncing capability with a medical device, and/or one or more structured tests. A given feature may include one or more parameters that can be configured. For example, the logbook may include a reminder setting for reminding the user to enter data into the logbook; a sync time/period for acquiring data from medical devices, such as a blood glucose monitor, an insulin pump, and/or a physical activity tracker; and/or a back-up setting for storing the data logged in the logbook to a memory located externally from the portable computing device having have the diabetes management application, such as the diabetes management system 12.

In the example embodiment, the diabetes management device 14 is described as being a medical device, such as a blood glucose monitor or an insulin pump, and/or a portable computing device with the diabetes management application residing in the portable computing device. The present disclosure may also be applicable to other electronic devices used to monitor diabetes, and is not limited to the examples described herein.

A user, such as a diabetes patient, may store data and access software tools supported by the diabetes management system 12. More particularly, using a computing device that communicates with the diabetes management system 12 via the communication network 22, the user may establish a user account and register as a client member with the diabetes management system 12. Through a user interface supported by the diabetes management system 12, the patient may create a profile that is stored by the diabetes management system 12. An exemplary client member profile may include the patient's name, the patient's address, and one or more health conditions of the patient. A client member profile may include other suitable information, and is not limited to the examples described herein.

Once registered, the user may authorize one or more healthcare providers registered with the diabetes management system 12 to access the user's profile. As an example, through the user interface, the user may search a database of healthcare providers registered with the diabetes management system 12. The user may send an invitation to a selected healthcare provider to link with the user. Once the selected healthcare provider accepts the user's invitation, the user may grant the selected healthcare provider permission to view and/or configure information related to the user's profile.

The diabetes management system 12 may associate the authorized healthcare provider with the user's profile. For example, the diabetes management system 12 can store the name of the healthcare provider and data indicating that the healthcare provider is approved by the user. Other suitable methods/techniques may be used to associate the user with the authorized healthcare provider.

The user may also register one or more diabetes management devices 14 as part of his/her profile with the diabetes management system 12. The user may be asked to provide device information that enables the diabetes management system 12 to identify and communicate with the diabetes management device 14. For example, the device information may include a nickname to be associated with the diabetes management device 14 (e.g., insulin pump, mobile phone 1), a serial number of the diabetes management device 14, a manufacturer of diabetes management device 14, an electronic mail address associated with the diabetes management device 14, and/or a transceiver address of the diabetes management device 14. The diabetes management system 12 stores the device information for each of the diabetes management devices 14 registered with the user's profile.

Before communicating with a registered diabetes management device, the diabetes management system 12 and the diabetes management device 14 may be paired with each other using well known communication protocols. As an example, the diabetes management system 12 may transmit a message that includes an identifier to the diabetes management device 14. Using the diabetes management device 14, the user may enter the identifier to initiate the pairing process, which may include verification of the inputted identifier as well as an exchange of authentication tokens (e.g., RSA keys) by the diabetes management system 12 and the diabetes management device 14. Once the tokens are validated, the pairing process is complete and the diabetes management system 12 and the diabetes management device 14 can automatically establish wireless communication with each other.

Once paired, the diabetes management device 14 and the diabetes management system 12 may exchange data with each other in accordance with a suitable communication protocol/standard (e.g., IEEE standard 11073). The diabetes management system 12 stores data received from the diabetes management device 14 as part of the user's profile. The registered diabetes management device may transmit information related to features of the diabetes management device 14, such as settings of one or more parameters. For example, if the diabetes management device 14 is an insulin pump, the insulin pump may transmit the values of one or more parameters used by a bolus calculator. In another example, if the diabetes management device 14 is a blood glucose monitor, the blood glucose monitor may transmit an activation status (i.e., ON/OFF) of one or more structured tests supported by the blood glucose monitor.

The healthcare provider, such as a primary care physician, may access the diabetes management system 12 by way of a computing device 26. For example, the computing device 26 may be a tablet, a smartphone, or a computer that includes a software application configured to communicate with the diabetes management system 12. In another example, the computing device 26 may access the diabetes management system 12 by way of a web-based interface that is run by the diabetes management system 12.

Similar to a patient with diabetes, the healthcare provider may have an user account with the diabetes management system 12. Specifically, the healthcare provider may register with the diabetes management system 12 as a healthcare provider member. For example, through a user interface supported by the diabetes management system 12, the healthcare provider may create a profile that is stored by the diabetes management system 12. An exemplary healthcare provider member profile may include the name of the healthcare provider, a work address of the healthcare provider, a specialization of the healthcare provider, and contact information (e.g., telephone number, e-mail address, web page address) of the healthcare provider.

In addition to the profile information, the diabetes management system 12 may request the healthcare provider to provide identification information to verify the credentials of the healthcare provider. Specifically, the identification information is used to verify the credentials of the healthcare provider as a professional authorized to diagnose and advise a patient with diabetes. An example of identification information includes the name of the healthcare provider, a license number, a work address, and/or names of hospitals/clinics that the healthcare provider is affiliated with. The identification information is stored by the diabetes management system 12 as part of the healthcare provider's profile.

Once registered, the healthcare provider may link with a patient who is also registered with the diabetes management system 12. For example, the healthcare provider may accept an invitation from the patient and/or request a registered patient to add him/her as an authorized healthcare provider. Once linked, the healthcare provider may view the patient's profile.

To assist in managing the patient's diabetes, the healthcare provider may configure an operation feature of a registered diabetes management device. In particular, the healthcare provider may issue a therapy setting that controls a given feature of a subject diabetes management device. The therapy setting may define settings for one or more parameters associated with the given feature. In one example, the therapy setting may adjust one or more parameters of a bolus calculator residing in an insulin pump. The parameters of the bolus calculator may include a target blood glucose level, insulin to carbohydrate ratio, insulin to blood glucose measure ratio, and/or maximum bolus. In another example, the therapy setting may activate/deactivate a structured test performed by a blood glucose meter. The therapy setting may identify the desired structured test (e.g., TiP and three-day profile structured test), and whether the desired structured test is to be turned ON or OFF. While specific diabetes management devices 14 and features/parameters were identified as being configured by a therapy setting, a therapy setting can be issued for other diabetes management devices 14 to configure other features/parameters.

The healthcare provider may issue the therapy setting by way of the diabetes management system 12. As an example, the healthcare provider may log into his/her account via the computing device 26. The diabetes management system 12 may display a user interface that includes a menu. The menu may include a therapy setting option. After selecting the therapy setting option, the healthcare provider may be prompted to enter information in multiple input fields. The input fields may request information for identifying the healthcare provider, validating the credentials of the healthcare provider, identifying the recipient of the therapy setting, identifying the diabetes management device 14 to be configured, and defining the feature/parameter of the diabetes management device 14 to be updated. Once completed, the information provided may be submitted as a therapy setting instruction to the diabetes management system 12.

To ensure that the healthcare provider is a professional authorized to diagnose and advise a diabetes patient, the diabetes management system 12 may validate the credentials of the healthcare provider by way of a third party, such as the physician validation system 18. In the example embodiment, the diabetes management system 12 transmits a validation request that includes the identification information of the healthcare provider to the physician validation system 18.

The physician validation system 18 may be housed in one or more servers, and is configured to determine whether a given healthcare provider is an authorized healthcare provider. For example, the physician validation system 18 may determine whether the license number of the healthcare provider is active in the state/country that issued the license. If the license number is active, the physician validation system 18 may notify the diabetes management system 12 that the credentials of the healthcare provider are valid. If the license number is not active, the physician validation system 18 may notify the diabetes management system 12 that the credentials of the healthcare provider are not valid. The physician validation system 18 may use various suitable methods for validating the credentials of the healthcare provider. An example of a physician validation system is Health Care Data Solution, which provides real-time physician verification service. The physician validation system 18 may also be referred to as a validation service.

Figure 3:
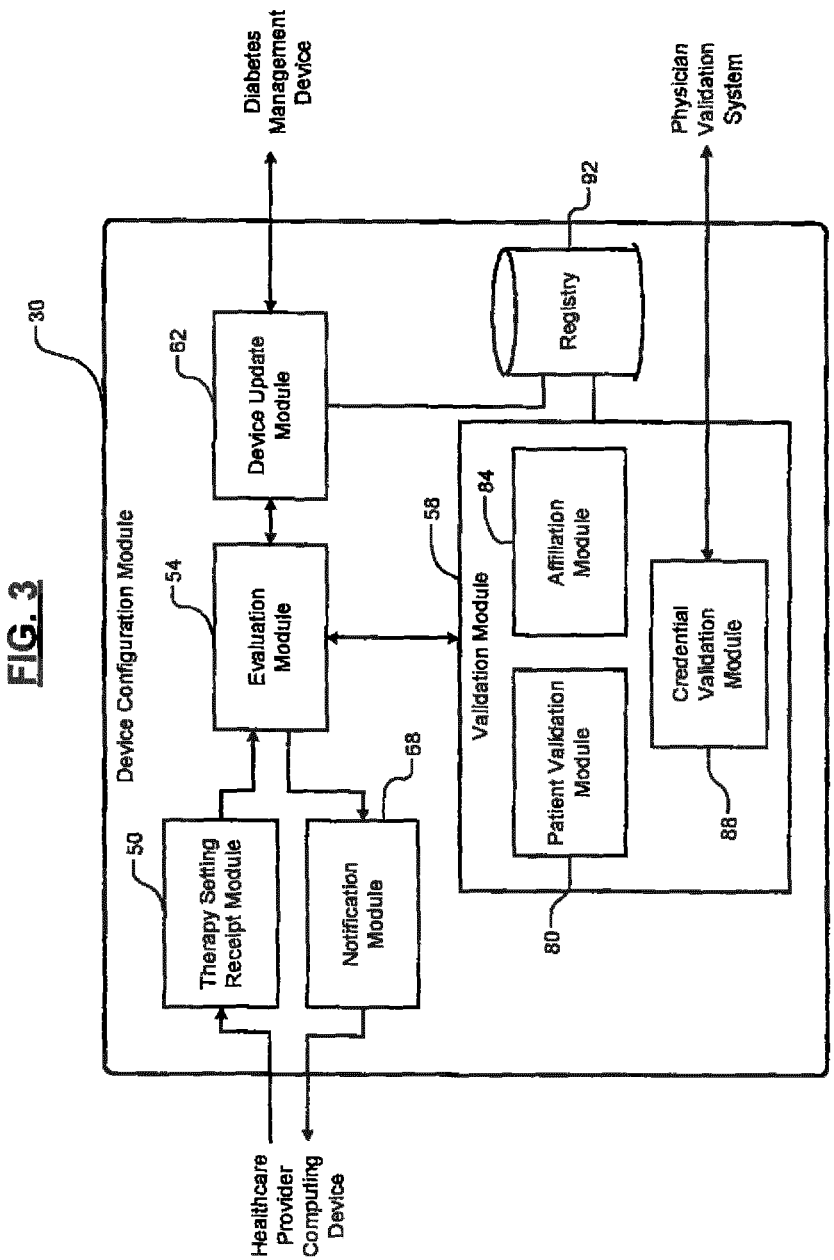
FIG. 3 is a block diagram of a device configuration module of the diabetes management system of the first embodiment.

The diabetes management system 12 includes a device configuration module 30 that processes a therapy setting request from the healthcare provider. With reference to FIG. 3, the device configuration module 30 includes a therapy setting receipt module 50, an evaluation module 54, a validation module 58, a device update module 62, and a notification module 66.

The therapy setting request module 50 receives a therapy setting instruction from the healthcare provider. For example, the healthcare provider may issue the therapy setting instruction by way of the user interface supported by the diabetes management system 12. The therapy setting instruction may include the identification information of the healthcare provider; information that identifies the patient receiving the therapy instruction, such as the name of the patient; and a therapy setting that identifies the diabetes management device 14 and the feature to be configured by the therapy setting.

The evaluation module 54 processes the therapy setting instruction received by the therapy setting receipt module 50. More particularly, based on the therapy setting instruction, the evaluation module 54 determines the sender of the instruction (i.e., the healthcare provider), the recipient of the instruction (i.e., the patient), and the diabetes management device 14 to be configured.

Before the therapy setting instruction is transmitted to the diabetes management device 14, the evaluation module 54 validates the healthcare provider and the patient by way of the validation module 58. More particularly, the evaluation module 54 determines if the patient and the healthcare provider are registered members of the diabetes management system 12, if the patient and the healthcare provider are associated with each other, and whether the healthcare provider is an active professional authorized to treat a person with diabetes.

The validation module 58 includes a patient validation module 80, an affiliation module 84, and a credential validation module 88. The patient validation module 80 determines whether the recipient (i.e., the patient) is registered with the diabetes management system 12. For example, the patient validation module 80 may compare the name of the recipient with the profiles of client members stored in a registry 92. The registry 92 may be a data store that stores profile information related to members registered with the diabetes management system 12. If the name of the recipient does not match the client members listed in the registry 92, the patient validation module 80 may notify the evaluation module 54 that the recipient is not a member of the diabetes management system 12. If the name of the recipient does match a client member listed in the registry 92, the patient validation module 80 may notify the affiliation module 84 that the recipient is a member of the diabetes management system 12.

The affiliation module 84 determines whether the healthcare provider is authorized by the client member to issue a therapy setting. For example, using the information in the registry 92, the affiliation module 84 may compare the name of the healthcare provider with the names of healthcare providers authorized by the client member. If the healthcare provider is listed as an authorized healthcare provider, the affiliation module 84 validates the relationship between the healthcare provider and the patient (i.e., the sender and the recipient). That is, the affiliation module 84 confirms that the healthcare provider is authorized by the client member to issue the therapy setting instruction. If the healthcare provider is not listed, the affiliation module 84 notifies the evaluation module 54 that the healthcare provider is not affiliated with the client member or, in other words, the healthcare provider is not authorized by the diabetes patient to issue the therapy setting instruction.

The credential validation module 88 validates the credentials of the healthcare provider. More particularly, the credential validation module 88 generates and transmits the validation request to the physician validation system 18. The validation request includes the identification information of the healthcare provider. The credential validation module 88 may retrieve the identification information from the therapy setting instruction and/or from the healthcare provider's profile. For example, the credential validation module 88 may compare the name of the healthcare provider with the profile of healthcare provider members stored in the registry and extract the identification information of the healthcare provider from the profile stored in the registry 92. The credential validation module 88 receives a report from the physician validation system 18 that indicates whether the credentials of the healthcare provider are valid or invalid. The credential validation module 88 notifies the evaluation module 54 of the result from the physician validation system 18.

The credential validation module 88 may perform the validation each time the healthcare provider issues a therapy setting instruction. Alternatively, the credential validation module 88 may perform the validation periodically. For example, if the healthcare provider issues multiple therapy settings in one day, the credential validation module 88 may perform the validation for the first instruction, after a predetermined time period has lapsed between two instructions, and/or for each time the healthcare provider logs into his/her account.

The device update module 62 generates and transmits a device configuration notification to the diabetes management device 14 to be configured. More particularly, based on the therapy setting instruction and the patient's profile, the device update module 62 determines whether the device 14 identified in the therapy setting instruction is registered with the diabetes management system 12. For example, the device update module 62 may compare the name of the device identified in the therapy setting with the device information of registered devices stored in the registry 92 with the client member's profile. If the device identified in the therapy setting is not listed as a registered device, the device update module 62 notifies the evaluation module 54 that the therapy setting instruction identifies an unregistered device.

If the device 14 is registered, the device update module 62 determines the feature to be adjusted by the therapy setting instruction and generates the device configuration notification. The device configuration notification includes information that informs the patient that a therapy setting has been issued by the healthcare provider. As an example, the device configuration notification may include the name of the healthcare provider issuing the therapy setting, details regarding the therapy setting issued (e.g., activate testing in pairs), and an execution instruction for accepting or declining and executing the therapy setting.

Figure 4:
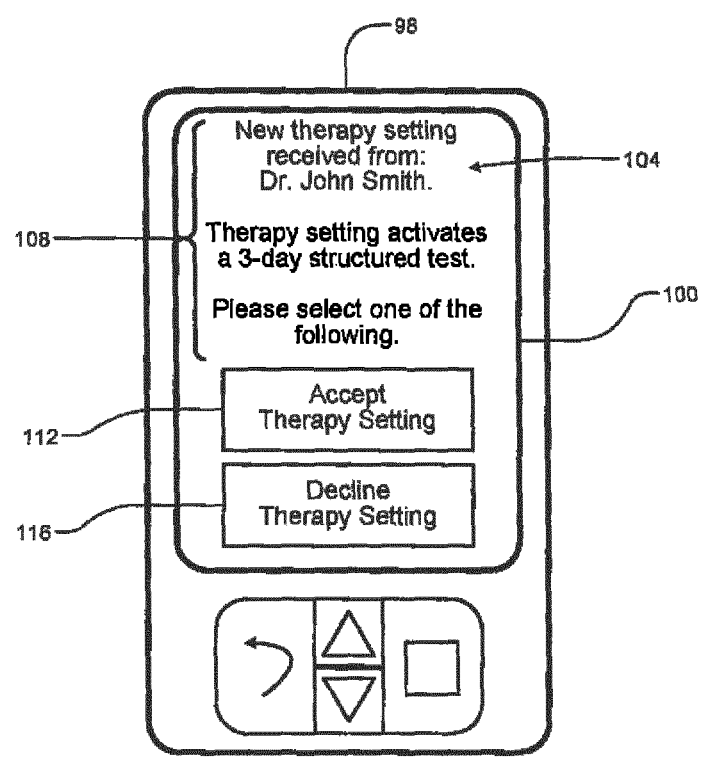
FIG. 4 illustrates a diabetes management device depicting a device configuration notification.

The device update module 62 transmits the device configuration notification to the diabetes management device 14 via the communication network 22, and the patient may access the device configuration notification via the diabetes management device 14. For example, FIG. 4 illustrates a blood glucose monitor 98 that includes a display 100, which may be a liquid crystal display. The display 100 presents a device configuration notification 104 that includes a message section 108, an accept button 112, and a decline button 116. The message section 108 presents information regarding the therapy setting from the healthcare provider, and requests the patient to either accept or decline the therapy setting by way of buttons 112 and 116. When one of the buttons 112 and 116 is operated, the blood glucose monitor 98 transmits a message to the diabetes management system 12 indicating whether the patient accepted or declined the therapy setting.

If the patient accepts the therapy setting by operating the accept button 112, the device update module 62 transmits the therapy setting to the diabetes management device 14 via the communication network 22. The therapy setting indicates the feature to be updated and/or the parameter value to be updated. For example, if the therapy setting is to activate a specific feature, the therapy setting identifies the structured test (e.g., TIP) and has the setting of the identified structured test as ON. In another example, if the therapy setting sets different parameters used by a bolus calculator, the therapy setting identifies each of the parameters and the value to be set for each of the parameters.

The device update module 64 may transmit the therapy setting in the form of an instruction that can be executed by the diabetes management device 14. Once the instructions are executed, the feature and/or parameters of the diabetes management device 14 are updated per the therapy setting. If the patient declines the therapy setting, the device update module 62 notifies the evaluation module 54 that the patient declined the therapy setting and, therefore, that the diabetes management device 14 was not updated.

To ensure that the patient or an individual authorized by the patient accepted the therapy setting, an activation code/key can be used to execute the instructions for updating the feature. For example, the diabetes management system 12 may assign an activation key to the therapy setting and provide the activation key to the healthcare provider via a message (e.g., e-mail message, SMS, pop-window as the healthcare provider is entering the therapy setting). The healthcare provider may relay the activation key to the patient by, for example, an email message, a SMS message, and/or telephone call.

To execute the update, the device update module 64 requires the patient to enter the activation key. That is, the instructions from the device update module 64 include an activation message and configuration instructions to configure the feature. The activation message, which is carried out by the diabetes management device 14, requests the patient to enter the activation key. Upon entering the assigned activation key, the instructions for configuring the feature are executed by the diabetes management device 14. If the entered key does not match the assigned activation key, the instruction for configuring the feature are not executed by the diabetes management device 14.

In some implementations, the diabetes management device 14 may verify whether the activation key received is in fact from a trusted source. For example, the verification may be performed using a hashing algorithm included in the diabetes management device 14. The healthcare provider may encrypt the activation key using the same hashing algorithm used by the diabetes management device 14. For example, the activation key may be generated by hashing identifying information of the patient (e.g., patient name, patient ID number) and an identifier associated with the diabetes management device 14 received via email or SMS message from the patient.

The diabetes management device 14 uses the hashing algorithm to decrypt the activation key when entered by the patient. The hashing algorithm in the diabetes management device 14 compares the decryption result to the identifying information entered into the diabetes management device 14 by the patient and/or the identifier associated with the diabetes management device 14. If the decryption result matches the identifying information of the patient and/or the identifier associated with the diabetes management device 14, the diabetes management device 14 determines, that the activation key is received from a trusted source and the instruction are executed. If the decryption result does not match the identifying information of the patient and/or the identifier associated with the diabetes management device 14, the diabetes management device 14 determines that the activation key is not received from a trusted source and the instructions are not executed.

The notification module 66 informs the healthcare provider of the status of the therapy setting instruction by transmitting a confirmation message to the healthcare provider via the communication network 22. For example, the confirmation message may indicate that the therapy setting instruction is invalid, that the therapy setting was accepted, or that the therapy setting was declined.

More particularly, when the validation module 58 determines that the healthcare provider is not registered, the healthcare provider is not authorized by the patient to issue the therapy setting, and/or that the credentials of the healthcare provider are invalid, the evaluation module 54 instructs the notification module 66 to notify the healthcare provider that the therapy setting instruction is invalid. The therapy setting instruction may also be invalid if the device update module 62 determines that the device 14 identified in the therapy instruction is not registered with the diabetes management system 12. The notification module 66 may specify the type of invalidation (i.e., unregistered patient, healthcare provider lacks authorization, invalid credentials, and/or unregistered device) in the confirmation message.

Furthermore, if the patient accepts the therapy setting, the evaluation module 54 instructs the notification module 66 to notify the healthcare provider that the therapy setting was accepted. Conversely, if the patient declines the therapy setting, the evaluation module 54 instructs the notification module 66 to notify the healthcare provider that the therapy setting was declined.

In the example embodiment, the device configuration module 30 receives a therapy setting instruction after the healthcare provider has submitted all of the information requested in the input fields of the user interface. Alternatively, the device configuration module 30 may process the therapy setting instruction as the healthcare provider is entering information in the input fields. For example, when the healthcare provider completes a patient identification field, the device configuration module 30 may determine whether the patient is a member of the diabetes management system 12 and whether the healthcare provider is associated with the patient who is a member. In yet another example, once the healthcare provider has logged into his/her account, the diabetes management system 10 may only display the therapy setting option for client members that have authorized the healthcare provider to issue the therapy setting. Accordingly, the diabetes management system 12 may be configured in multiple ways for receiving and evaluating the therapy setting from the healthcare provider.

Figure 5:
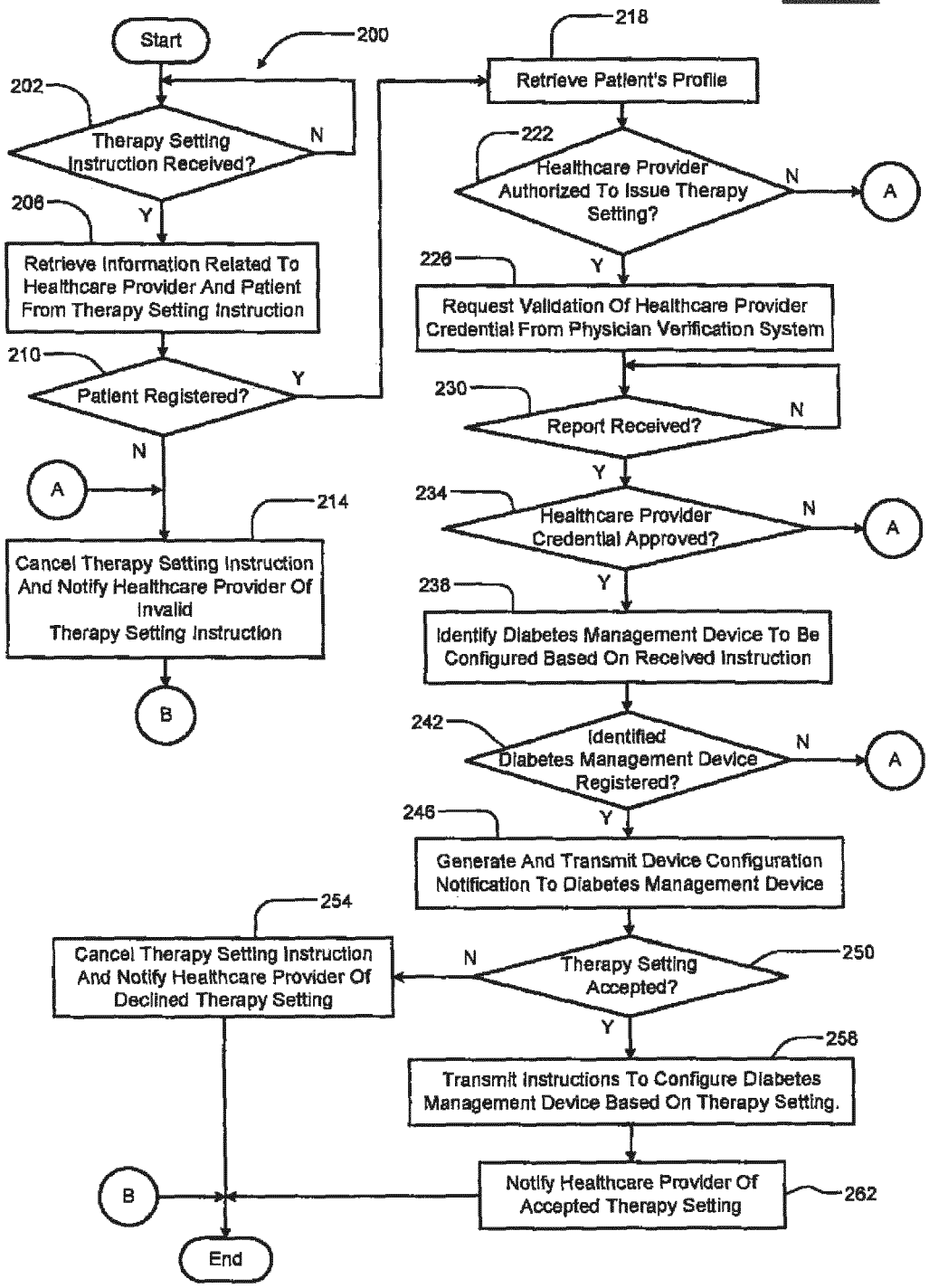
FIG. 5 is a flowchart illustrating an example routine performed by the device configuration module for processing a therapy setting instruction.

With reference to FIG. 5, an example of a device configuration routine 200 is presented. The device configuration routine 200 may be performed by the device configuration module 30 of the diabetes management system 12. At 202, the device configuration module 30 determines whether a therapy setting instruction has been received. If no instruction has been received, the module 30 returns to 202. If an instruction has been received, the module 30, at 206, retrieves information related to the healthcare provider (i.e., the sender) and the patient (i.e., recipient) from the therapy setting instruction received. At 210, the module 30 determines whether the patient is registered with the diabetes management system 12. If the patient is not registered, the module 30 cancels the therapy setting instruction and notifies the healthcare provider that the therapy setting instruction is invalid at 214. For example, the module 30 may transmit a confirmation message to the healthcare provider via the communication network 22. The confirmation message may indicate that the therapy setting instruction is invalid because the patient is not registered with the diabetes management system 12.

If the patient is registered, the module 30 retrieves the profile of the patient at 218 and determines whether the healthcare provider is authorized by the patient to issue a therapy setting at 222. If the healthcare provider is not authorized to issue the therapy setting, the module 30 cancels the instruction and notifies the healthcare provider that the therapy setting instruction is invalid, at 214, via the confirmation message. The confirmation message may indicate that the therapy setting instruction is invalid because the healthcare provider is not authorized by the patient to issue the therapy setting.

If the healthcare provider is authorized, the module 30 requests the physician validation system 18 to validate the healthcare provider's credentials at 226. For example, the module 30 may transmit a validation request that includes a name and a license number of the healthcare provider to the physician validation system 18. At 230, the module 30 determines whether a report from the physician validation system 18 has been received. If no report has been received, the module 30 returns to 230. If a report has been received, the module 30 determines whether the healthcare provider's credentials are valid based on the report at 234. If the healthcare provider's credentials are invalid, the module 30 cancels the instruction and notifies the healthcare provider that the therapy setting instruction is invalid via the confirmation message at 214. The confirmation message may indicate that the therapy setting instruction is invalid because the credentials of healthcare provider are invalid.

If the healthcare provider's credentials are valid, the module 30, at 238, identifies the diabetes management device 14 to be configured based on the therapy setting instruction. At 242, the module 30 determines whether the identified device is registered with the diabetes management system 12. For example, the module 30 checks the patient's profile to determine if the identified device is registered. If the identified device is not registered, the module 30 cancels the instruction and notifies the healthcare provider that the therapy setting instruction is invalid via the confirmation message at 214. The confirmation message may indicate that the therapy setting instruction is invalid because the diabetes management device 14 is not registered.

If the identified device is registered, the module 30 generates a device configuration notification and transmits the notification to the diabetes management device 14 at 246. The device configuration notification notifies the patient that a therapy setting for the diabetes management device 14 has been received, and asks the patient to either accept or decline the therapy setting. At 250, the module 30 determines whether the therapy setting is accepted by the patient. For example, if the patient operates one of the buttons 112 and 114, the diabetes management device 14 transmits a message to the diabetes management system 12 via the communication network 22 indicating that the therapy setting is accepted or declined based on the button operated.

If the patient declines the therapy setting, the module 30 cancels the instruction and notifies the healthcare provider that the therapy setting has been declined at 254. Alternatively, if the patient accepts the therapy setting, the module 30 transmits computer executable instructions to the diabetes management device 14 for updating the diabetes management device 14 according to the therapy setting, at 258, and notifies the healthcare provider that the therapy setting was accepted at 262. The diabetes management device 14 executes the instructions from the diabetes management system 12 to update the operation feature indicated in the therapy setting.

In the first embodiment of the therapy setting system 10, the diabetes management system 12 receives a therapy setting instruction from the healthcare provider and verifies the credentials of the healthcare provider by way of the physician validation system 18. In a second embodiment, the credentials of the healthcare provider are validated by a prescription system before the therapy setting is received by the diabetes management system 12.

Figure 6:
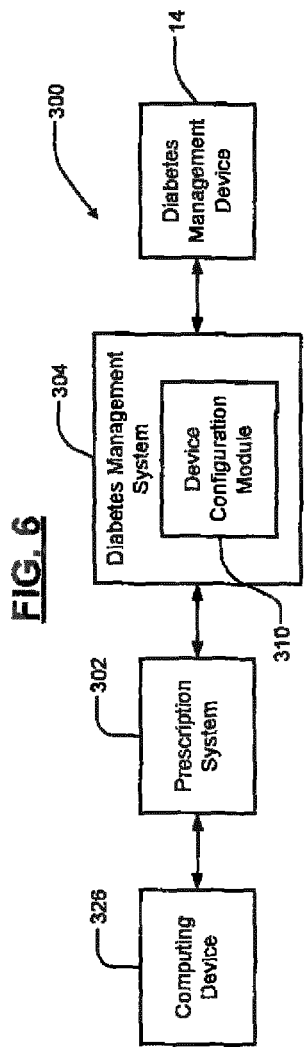
FIG. 6 is a block diagram of a therapy setting system that includes a diabetes management system and a prescription system in a second embodiment.

More particularly, with reference to FIG. 6, an example functional block diagram of a therapy setting system 300 in a second embodiment is presented. Similar to the first embodiment, the therapy setting system 300 enables the healthcare provider to configure the diabetes management device 14 of the patient. In the second embodiment, a prescription system 302 facilitates in the processing of the therapy setting instruction by validating the credentials of the healthcare provider and forwarding the therapy setting to a diabetes management system 304.

The prescription system 302 exchanges data with the computing device 26 of the healthcare provider and the diabetes management system 304 by way of a communication network (e.g., the Internet) 22. The prescription system 302 may be an electronic prescribing system that receives electronic prescriptions from the healthcare provider. The healthcare provider may be registered as a member with the prescription system 302. The healthcare provider may submit identification information that allows the prescription system 302 to identify and validate the credentials of the healthcare provider, such as a name of the healthcare provider, a license number of the healthcare provider, and/or other suitable information.

The prescription system 302 may maintain a database of registered healthcare providers, and may validate the credentials of each healthcare provider each time the healthcare provider issues a prescription or periodically. For example, if the healthcare provider issues multiple prescriptions in one day, the prescription system 302 may perform the validation only for the first prescription or after a predetermined time period has lapsed between two prescriptions. If the credentials of the healthcare provider are valid, the prescription system 302 may process the prescription submitted and notify the healthcare provider of the status of the prescription. Conversely, if the credentials of the healthcare provider are invalid, the prescription system 302 may notify the healthcare provider that the prescription cannot be filled because the healthcare provider does not have the proper credentials for issuing the prescription.

The healthcare provider may issue a therapy setting instruction as a prescription to the prescription system 302. The prescription system 302 is configured to determine if the issued prescription prescribes a medicine or a therapy setting for a diabetes management device 14. For example, the prescription may have a field that identifies the prescription as a therapy setting or medicine. As another example, the prescription system 302 may determine the type of prescription based on the recipient. That is, the healthcare provider may identify the recipient of the prescription as the diabetes management system 304 or as a pharmacy. The prescription system 302 may identify the prescription as a therapy setting when the diabetes management system 304 is the recipient and as a medicine when the pharmacy is the recipient. In the event that the prescription is a therapy setting instruction, the prescription system 302 forwards the therapy setting instruction to the diabetes management system 304 via the communication network 22.

Figure 7:
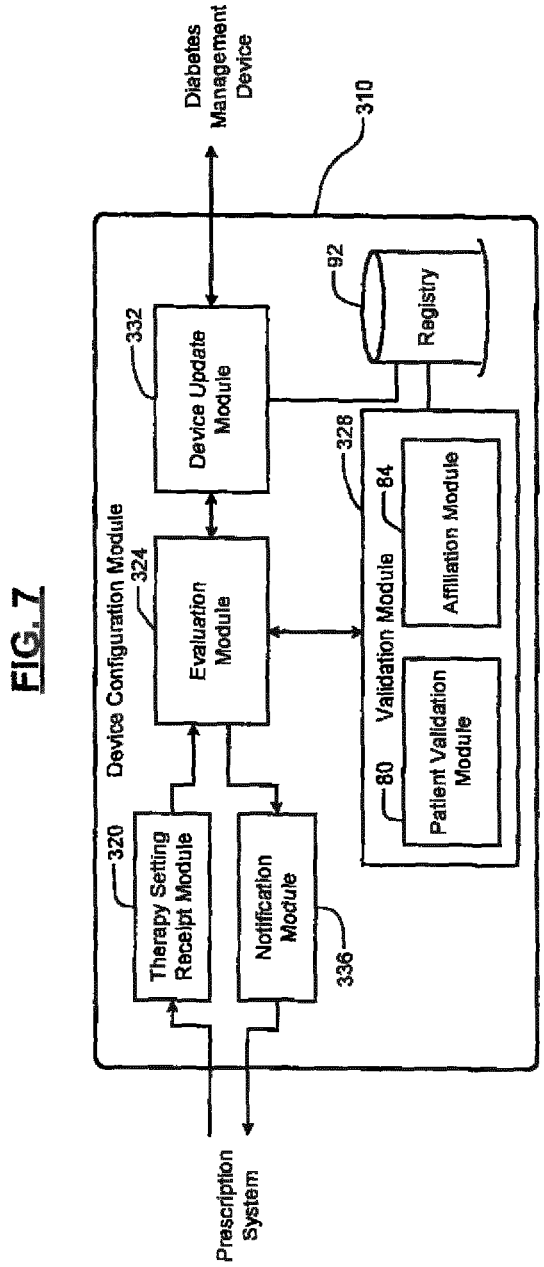
FIG. 7 is a block diagram of a device configuration module of the diabetes management system of the second embodiment.

The diabetes management system 304 includes a device configuration module 310 for processing the therapy setting instruction from the prescription system 302. With reference to FIG. 7, an example block diagram of the device configuration module 310 is presented. The device configuration module 310 is similar to the device configuration module 30 of the first embodiment, but does not include the credential validation module 88. More particularly, the diabetes configuration module 310 includes a therapy setting receipt module 320, an evaluation module 324, a validation module 328, a device update module 332, and a notification module 336.

The therapy setting receipt module 320, the evaluation module 324, the validation module 328, the device update module 332, and the notification module 336 function in a similar manner as the therapy setting receipt module 50, the evaluation module 54, the validation module 58, the device module update 62, and the notification module 66 of the first embodiment, respectively. Differences between the modules of the first embodiment and the second embodiment are described further below.

Instead of receiving the therapy setting instruction from the healthcare provider, the therapy setting request module 320 receives the therapy setting instruction from the prescription system 302. In particular, the prescription system 302 forwards the prescription, which includes the therapy setting instruction, to the diabetes management system 304 when the credentials of the healthcare provider are deemed valid.

Before the therapy setting instruction is transmitted to the diabetes management device 14, the evaluation module 324 has the validation module 328 determine if the patient and the healthcare provider are registered members of the diabetes management system and if the patient and the healthcare provider are associated with each other. Since the prescription system 302 validated the credentials of the healthcare provider, the validation module 328 no longer determines whether the healthcare provider is an active professional authorized to treat a person with diabetes. Accordingly, the validation module 328 includes the patient validation module 80 and the affiliation module 84.

Similar to the first embodiment, the device update module 332 generates and transmits the device configuration notification to the diabetes management device 14 that is to be configured and is registered by the patient. If the patient accepts the therapy setting, the device update module 332 transmits instructions to the diabetes management device 14 to configure the device 14 according to the therapy setting. If the patient declines the therapy setting, the device update module 332 notifies the evaluation module 324 that the patient declined the therapy setting and, therefore, that the diabetes management device 14 was not configured.

The notification module 336 informs the prescription system 302 of the status of the therapy setting instruction by transmitting a confirmation message to the prescription system 302 via the communication network 22. For example, the confirmation message may indicate that the therapy setting instruction is invalid, that the therapy setting was accepted, or that the therapy setting was declined.

More particularly, when the validation module 328 determines that the healthcare provider is not registered, the healthcare provider is not authorized by the patient to issue the therapy setting, and/or the device 14 is not registered, the evaluation module 324 instructs the notification module 336 to notify the prescription system 302 that the therapy setting instruction is invalid. In addition, if the patient accepts the therapy setting, the evaluation module 324 instructs the notification module 336 to notify the prescription system 302 that the therapy setting was accepted. Conversely, if the patient declines the therapy setting, the evaluation module 324 instructs the notification module 336 to notify the prescription system 302 that the therapy setting was declined. The prescription system 302 forwards the notification from the notification module 336 to the healthcare provider.

Figure 8:
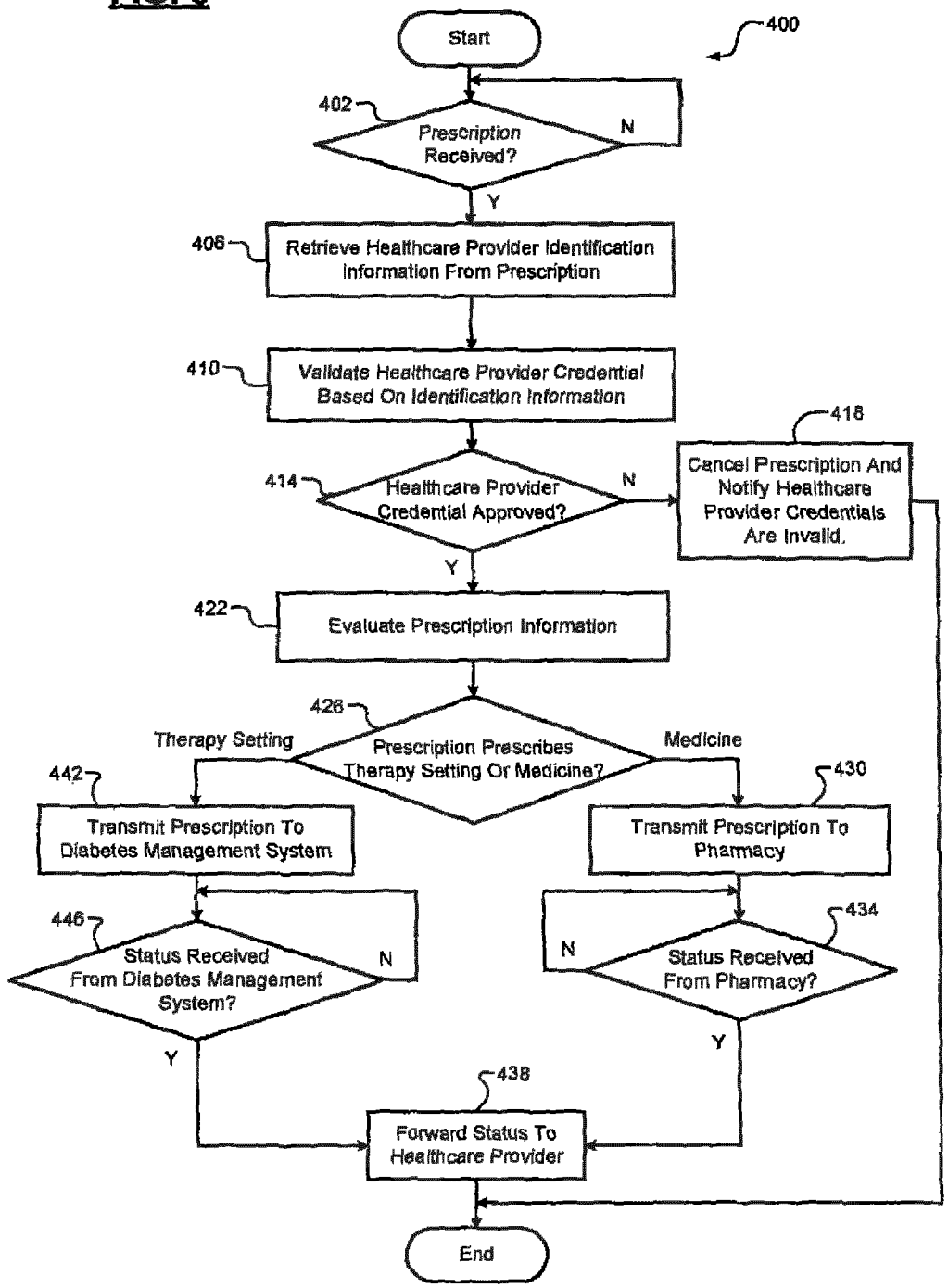
FIG. 8 is a flowchart illustrating an example routine performed by the prescription system for processing a prescription.

With reference to FIG. 8, an example of a prescription process routine 400 is presented. The prescription process routine 400 is performed by the prescription system 302. At 402, the prescription system 302 determines whether a prescription has been received. If no prescription has been received, the system 302 returns to 402. If a prescription has been received, the system 302 retrieves the healthcare provider's identification information from the prescription at 406. At 410, the system 302 validates the credentials of the healthcare provider. Various methods may be used by the prescription system 302 to validate the credentials of the healthcare provider.

At 414, the system 302 determines whether the healthcare provider's credentials are valid based on the analysis at 410. If the healthcare provider's credentials are invalid, the system 302, at 418, cancels the prescription and notifies the healthcare provider that the prescription cannot be filled because the healthcare provider is not authorized to issue the prescription.

If the healthcare provider's credentials are valid, the system 302 evaluates the prescription at 422 and determines if the prescription prescribes a therapy setting or medicine at 426. For example, if the recipient of the prescription is a pharmacy, the prescription system determines that the prescription prescribes medicine. If the recipient of the prescription is the diabetes management system 304, the system 302 determines that the prescription prescribes a therapy setting. Other methods may be used to determine if the prescription prescribes a therapy setting or a medicine.

If the prescription prescribes a medicine, the system 302 transmits the prescription to the pharmacy at 430. At 434, the system 302 determines whether a status of the prescription has been received from the pharmacy. For example, the pharmacy may notify the system 302 when the prescription has been filled and/or picked up by the patient. If the status has been received, the system 302 forwards the status to the healthcare provider at 438. If the status has not been received, the system 302 returns to 434.

If the prescription prescribes a therapy setting, the system 302 transmits the prescription to the diabetes management system 304 at 442. At 446, the system 302 determines whether a status of the prescription has been received from the diabetes management system 304. For example, the diabetes management system 304 may transmit the confirmation message to the system 302 as a status of the therapy setting. If the status has been received, the system 302 forwards the status to the healthcare provider at 438. If the status has not been received, the system 302 returns to 446.

Figure 9:
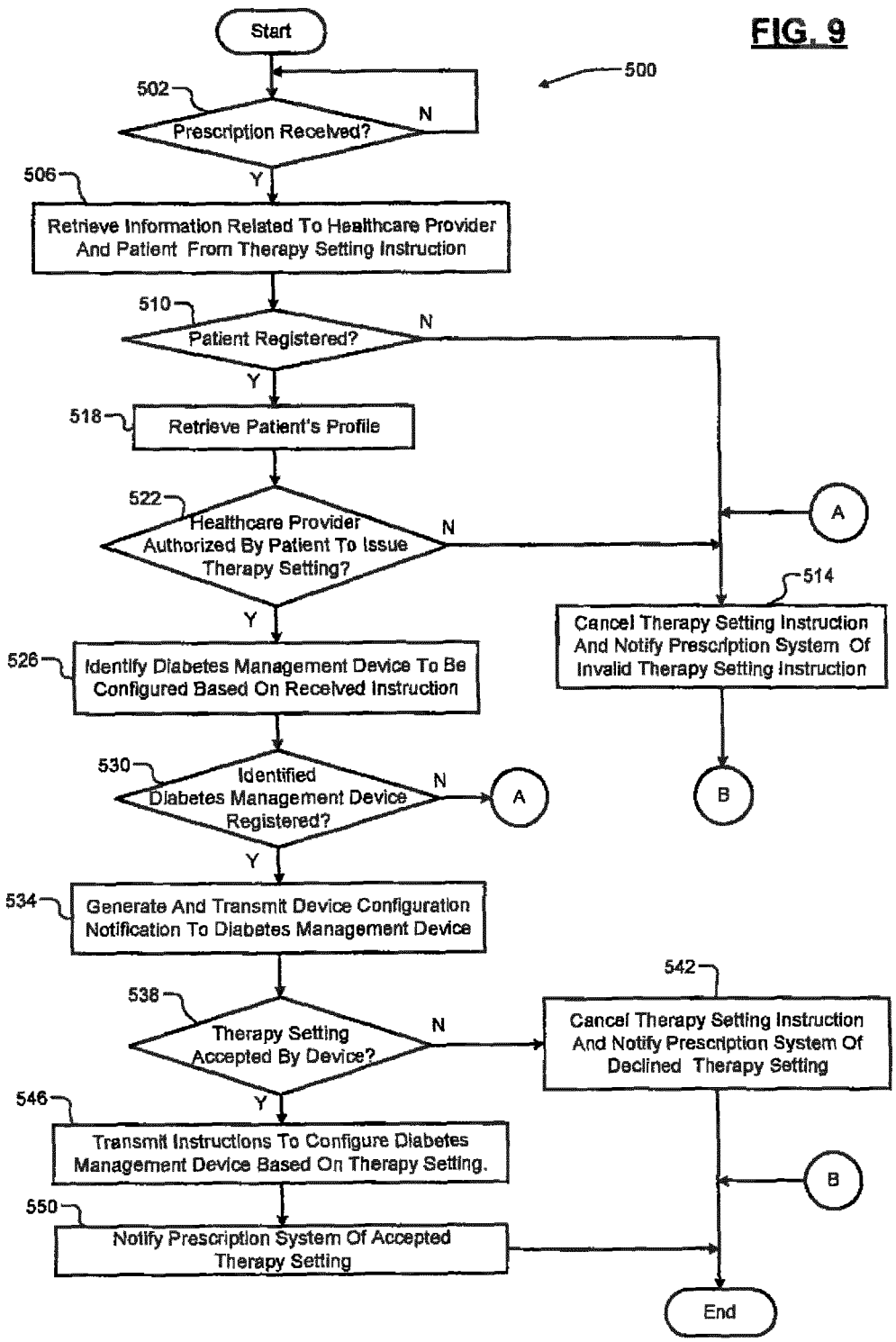
FIG. 9 is a flowchart illustrating an example routine performed by the device configuration module of the second embodiment for processing a therapy setting instruction from the prescription system.

With reference to FIG. 9, a device configuration routine 500 is presented. The device configuration routine 500 may be performed by the device configuration module 310 of the diabetes management system 304. At 502, the module 310 determines whether a prescription has been received. More particularly, the module 310 determines whether a therapy setting instruction is received from the prescription system 302.

If no instruction has been received, the module 310 returns to 502. If an instruction has been received, the module 310, at 506, retrieves information related to the healthcare provider and the patient from the therapy setting instruction. At 510, the module 310 determines whether the patient is registered with the diabetes management system 304. If the patient is not registered, the module 310 cancels the instruction and notifies the prescription system 302 that the therapy setting instruction is invalid at 514. For example, the module 310 may transmit the confirmation message to the prescription system 302 via the communication network 22. The confirmation message may indicate that the therapy setting instruction is invalid because the patient is not registered with the diabetes management system 304.

If the patient is registered, the module 310 retrieves the profile of the patient, at 518, and determines whether the healthcare provider is authorized by the patient to issue a therapy setting at 522. If the healthcare provider is not authorized to issue the therapy setting, the module 310 cancels the instruction and notifies the prescription system 302 that the therapy setting instruction is invalid, at 514, by way of the confirmation message. The confirmation message may indicate that the therapy setting instruction is invalid because the healthcare provider is not authorized by the patient to issue the therapy setting.

If the healthcare provider is authorized, the module 310, at 526, identifies the diabetes management device to be configured based on the therapy setting instruction. At 530, the module 310 determines whether the identified device is registered with the diabetes management system 304. If the identified device is not registered, the module 310 cancels the instruction and notifies the healthcare provider that the therapy setting instruction is invalid via the confirmation message at 514. If the identified device is registered, the module 310 generates a device configuration notification and transmits the notification to the diabetes management device 14 at 534.

At 538, the module 310 determines whether the therapy setting is accepted by the patient. If the patient declines the therapy setting, the module 310 cancels the instruction and notifies the prescription system 302 that the therapy setting has been declined at 542. Alternatively, if the patient accepts the therapy setting, the module 310 transmits instruction to the diabetes management device 14 for executing the therapy setting, at 546, and notifies the prescription system 302 that the therapy setting was accepted at 550.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth, such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail.

In this application, including the definitions below, the term "module" or the term "controller" may be replaced with the term "circuit." The term "module" may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The invention claimed is:

1. A device configuration method for configuring a diabetes management device by a diabetes management system, the diabetes management system residing on a server computer, the method comprising:
receiving, by the diabetes management system, a therapy setting instruction from a computing device, wherein the therapy setting instruction includes a therapy setting, an identification information of a healthcare provider, and a recipient information, the therapy setting includes information to configure a feature of a desired diabetes management device, the identification information includes information to validate credentials of the healthcare provider, the recipient information includes information to identify a patient of the healthcare provider that is a user of the desired diabetes management device, the diabetes management system is in data communication with the computing device via a communication network, and the computing device is operable by the healthcare provider;
determining, by the diabetes management system, a time period between receipt of the therapy setting instruction and another therapy setting instruction, where the another therapy setting instruction is most recently received therapy setting instruction prior to the therapy setting instruction;
validating, by the diabetes management system, the credentials of the healthcare provider by way of a validation service based on the identification information, wherein the validation is only performed when the time period exceeds a predetermined time period and wherein the validation service is a third party different from the diabetes management system;
identifying, by the diabetes management system, a subject diabetes management device to be configured based on the therapy setting instruction;
determining, by the diabetes management system, whether the therapy setting instruction is valid based on an association between the diabetes management system, the patient, and the healthcare provider;
transmitting, by the diabetes management system, one or more parameters for configuring the feature configured by the therapy setting to the subject diabetes management device in response to the credentials of the healthcare provider being valid and the therapy setting instruction being valid, wherein the diabetes management system is in data communication with the subject diabetes management device via the communication network and the subject diabetes management device executes the feature configured with the one or more parameters;
canceling, by the diabetes management system, the therapy setting instruction in response to the therapy setting instruction being invalid; and
administering insulin, by the subject diabetes management device, in response to the therapy setting instruction being valid.

2. The device configuration method of claim 1 the method further comprising:
comparing, by the diabetes management system, the recipient information provided in the therapy setting instruction with a profile information of one or more registered members stored in a registry, wherein the diabetes management system includes the registry;
classifying, by the diabetes management system, the patient as a subject registered member in response to the recipient information corresponding with the profile information of at least one of the one or more registered members; and
identifying, by the diabetes management system, the therapy setting instruction as invalid in response to the recipient information not corresponding with the profile information of at least one of the one or more registered members.

3. The device configuration method of claim 2 further comprising:
determining, by the diabetes management system, whether the healthcare provider is authorized by the subject registered member to issue the therapy setting instruction in response to the patient being registered with the diabetes management system, wherein the diabetes management system is operable by the subject registered member to identify an authorized healthcare provider and the diabetes management system stores information to associate the authorized healthcare provider with the subject registered member; and
identifying, by the diabetes management system, the therapy setting instruction as invalid in response to the healthcare provider not being authorized by the subject registered member.

4. The device configuration method of claim 2 further comprising:
determining, by the diabetes management system, whether the subject diabetes management device identified is registered with the diabetes management system by the subject registered member in response to the patient being registered with the diabetes management system, wherein the diabetes management system is operable by the subject registered member to register a given diabetes management device and the diabetes management system stores information regarding the given diabetes management device with the profile information of the subject registered member; and
identifying, by the diabetes management system, the therapy setting instruction as invalid in response to the diabetes management device not being registered with the diabetes management system.

5. The device configuration method of claim 1 further comprising:
prior to transmitting the one or more parameters, issuing, by the diabetes management system, a device configuration notification to the subject diabetes management device in response to the credentials of the healthcare provider being valid and the therapy setting instruction being valid, wherein the device configuration notification notifies the user that the healthcare provider has issued the therapy setting and requests the user to either accept or decline the therapy setting; and receiving, by the diabetes management system, a message from the subject diabetes management device via the communication network, wherein the message indicates whether the user accepts or declines the therapy setting; and canceling, by the diabetes management system, the therapy setting instruction in response to the message indicating the user declined the therapy setting instruction, wherein the diabetes management system transmits the one or more parameters in response to the message indicating the user accepted the therapy setting instruction.

6. The device configuration method of claim 5 further comprising:

notifying, by the diabetes management system, the healthcare provider of a status of the therapy setting instruction, wherein the status of the therapy setting is designated as an accepted therapy setting in response to the therapy setting being accepted by the user, the status of the therapy setting is designated as a declined therapy setting in response to the therapy setting being declined by the user, and the status of the therapy setting is designated as invalid in response to the credentials of the healthcare provider being invalid.

7. The device configuration method of claim 1 wherein the identification information includes at least one of a name of the healthcare provider and a license number of the healthcare provider.

8. The device configuration method of claim 1 wherein the diabetes management device is a medical device.

9. The device configuration method of claim 1 wherein the diabetes management device is a portable computing device that has a diabetes management application residing in the portable computing device.

10. The device configuration method of claim 1 wherein the therapy setting instruction is determined as invalid in response to the credentials of the healthcare provider being invalid.

11. The device configuration method of claim 1 wherein the diabetes management system is paired with the subject diabetes management device before transmitting the one or more parameters such that the diabetes management system and the subject diabetes management device automatically communicate via the communication network.

* * * * *